US010149760B2

United States Patent
Johnson et al.

(10) Patent No.: US 10,149,760 B2
(45) Date of Patent: Dec. 11, 2018

(54) ASSEMBLY AND METHOD FOR LOADING A SELF-EXPANDING COLLAPSIBLE HEART VALVE

(71) Applicant: St. Jude Medical, Cardiology Division, Inc., St. Paul, MN (US)

(72) Inventors: Michael A. Johnson, Savage, MN (US); Valerie J. Glazier, Eden Prairie, MN (US); Huisun Wang, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/296,799

(22) Filed: Oct. 18, 2016

(65) Prior Publication Data
US 2017/0035570 A1   Feb. 9, 2017

Related U.S. Application Data

(60) Continuation of application No. 14/575,175, filed on Dec. 18, 2014, now Pat. No. 9,492,274, which is a
(Continued)

(51) Int. Cl.
*B23P 19/00*   (2006.01)
*A61F 2/24*   (2006.01)
(Continued)

(52) U.S. Cl.
CPC .............. *A61F 2/2436* (2013.01); *A61F 2/24* (2013.01); *A61F 2/2418* (2013.01);
(Continued)

(58) Field of Classification Search
CPC ................................... B23P 11/00; A61F 2/24
See application file for complete search history.

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| EP | 1129744 A1 | 9/2001 |
| EP | 1157673 A2 | 11/2001 |

(Continued)

OTHER PUBLICATIONS

Ruiz, Carlos, Overview of PRE-CE Mark Transcatheter Aortic Valve Technologies, Euro PCR, dated May 25, 2010.
(Continued)

*Primary Examiner* — Lee D Wilson
(74) *Attorney, Agent, or Firm* — Lerner, David, Littenberg, Krumholz & Mentlik, LLP

(57) ABSTRACT

An assembly for collapsing a prosthetic heart valve includes a compression member and a pusher member. The compression member has a first open end with a first diameter, a second open end with a second diameter less than the first diameter, and a tapered wall between the first open end and the second open end. The pusher member has a base adapted to engage an end of the valve. The pusher member and the compression member are movable relative to one another between an initial position in which the base of the pusher member is relatively far from the first open end of the compression member and an operative position in which the base of the pusher member is relatively close to the first open end of the compression member. Movement of the pusher and compression members from the initial position to the operative position radially compresses the valve.

9 Claims, 13 Drawing Sheets

Related U.S. Application Data division of application No. 13/234,688, filed on Sep. 16, 2011, now Pat. No. 8,973,234.

(60) Provisional application No. 61/383,908, filed on Sep. 17, 2010.

(51) Int. Cl.
*B23P 11/02* (2006.01)
*A61F 2/95* (2013.01)

(52) U.S. Cl.
CPC ........... *A61F 2/2427* (2013.01); *B23P 11/025* (2013.01); *A61F 2/2412* (2013.01); *A61F 2002/9522* (2013.01); *A61F 2210/0014* (2013.01); *A61F 2210/0028* (2013.01); *A61F 2250/0039* (2013.01); *Y10T 29/49863* (2015.01); *Y10T 29/49865* (2015.01); *Y10T 29/49927* (2015.01); *Y10T 29/53909* (2015.01); *Y10T 137/0402* (2015.04)

(56) References Cited

U.S. PATENT DOCUMENTS

| | | | |
|---|---|---|---|
| 5,843,167 A | 12/1998 | Dwyer et al. | |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,132,458 A | 10/2000 | Staehle et al. | |
| 6,306,141 B1 | 10/2001 | Jervis | |
| 6,471,718 B1 | 10/2002 | Staehle et al. | |
| 6,623,518 B2 | 9/2003 | Thompson et al. | |
| 6,814,746 B2 | 11/2004 | Thompson et al. | |
| 6,830,584 B1 | 12/2004 | Seguin | |
| 6,935,389 B1 | 8/2005 | Rinaldi | |
| 7,014,074 B1 | 3/2006 | Rinaldi | |
| 7,018,406 B2 | 3/2006 | Seguin et al. | |
| 7,096,554 B2 | 8/2006 | Austin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 8,561,967 B2 | 10/2013 | Hendriksen et al. | |
| 8,562,663 B2 | 10/2013 | Mearns et al. | |
| 8,585,019 B2 * | 11/2013 | Melsheimer | A61F 2/95 |
| | | | 254/134.3 FT |
| 8,931,159 B2 | 1/2015 | Hillukka | |
| 8,973,234 B2 * | 3/2015 | Johnson | A61F 2/2418 |
| | | | 29/270 |
| 9,192,469 B2 | 11/2015 | Mearns et al. | |
| 9,414,914 B2 | 8/2016 | Duffy et al. | |
| 9,414,917 B2 | 8/2016 | Young et al. | |
| 9,492,274 B2 * | 11/2016 | Johnson | A61F 2/2418 |
| 9,675,456 B2 * | 6/2017 | Quill | A61F 2/2436 |
| 2002/0096468 A1 | 7/2002 | Zuk | |
| 2003/0050694 A1 | 3/2003 | Yang et al. | |
| 2003/0070682 A1 | 4/2003 | Wilson et al. | |
| 2004/0210304 A1 | 10/2004 | Seguin et al. | |
| 2005/0137695 A1 | 6/2005 | Salahieh et al. | |
| 2005/0137697 A1 | 6/2005 | Salahieh et al. | |
| 2005/0194578 A1 | 9/2005 | Morris | |
| 2006/0074484 A1 | 4/2006 | Huber | |
| 2006/0106415 A1 | 5/2006 | Gabbay | |
| 2006/0135973 A1 * | 6/2006 | Hawkins | A61B 17/3415 |
| | | | 606/167 |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2007/0270931 A1 | 11/2007 | Leanna et al. | |
| 2007/0270932 A1 | 11/2007 | Headley et al. | |
| 2008/0071369 A1 | 3/2008 | Tuval et al. | |
| 2008/0147182 A1 | 6/2008 | Righini et al. | |
| 2008/0221703 A1 | 9/2008 | Que et al. | |
| 2009/0054975 A1 | 2/2009 | del Nido et al. | |
| 2009/0093876 A1 | 4/2009 | Nitzan et al. | |
| 2009/0143857 A1 | 6/2009 | Melsheimer et al. | |
| 2010/0004740 A1 | 1/2010 | Seguin et al. | |
| 2010/0051886 A1 | 3/2010 | Cooke et al. | |
| 2010/0286768 A1 | 11/2010 | Alkhatib | |
| 2010/0298931 A1 | 11/2010 | Quadri et al. | |
| 2011/0224678 A1 | 9/2011 | Gabbay | |
| 2012/0078352 A1 | 3/2012 | Wang et al. | |
| 2012/0083875 A1 * | 4/2012 | Johnson | A61F 2/2427 |
| | | | 623/2.11 |
| 2012/0330408 A1 | 12/2012 | Hillukka et al. | |
| 2013/0190859 A1 | 7/2013 | Hillukka | |
| 2014/0331475 A1 | 11/2014 | Duffy et al. | |
| 2015/0101171 A1 * | 4/2015 | Johnson | A61F 2/2427 |
| | | | 29/446 |
| 2016/0278955 A1 | 9/2016 | Liu et al. | |
| 2017/0035570 A1 * | 2/2017 | Johnson | A61F 2/2427 |

FOREIGN PATENT DOCUMENTS

| | | |
|---|---|---|
| JP | 2000093523 A | 4/2000 |
| JP | 2009-533139 | 9/2009 |
| WO | 07071436 A2 | 6/2007 |
| WO | 2007081940 A2 | 7/2007 |
| WO | 2007120543 A1 | 10/2007 |
| WO | 08070797 A2 | 6/2008 |
| WO | 2009091509 A1 | 7/2009 |
| WO | 2010014834 A1 | 2/2010 |
| WO | 10051025 A1 | 5/2010 |
| WO | 10087975 A1 | 8/2010 |
| WO | 10096176 A1 | 8/2010 |
| WO | 2012023979 A2 | 2/2012 |
| WO | 2012036742 A2 | 3/2012 |
| WO | 2012036744 A2 | 3/2012 |
| WO | 2012057983 A1 | 5/2012 |
| WO | 2012106491 A1 | 8/2012 |

OTHER PUBLICATIONS

International Search Report and Written Opinion for Application No. PCT/US2012/023576 dated Jul. 6, 2012.
International Search Report for Application No. PCT/US2012/048307 dated Feb. 28, 2013.
International Search Report for Application No. PCT/US2012/048298 dated Nov. 7, 2012.
Quaden et al., "Percutaneous aortic valve replacement: resection before implantation", pp. 836-840, European J. of Cardio-thoracic Surgery, 27 (2005).
International Search Report for Application No. PCT/US2011/001598 dated Jul. 6, 2012.
Medtronic, "CoreValve Percutaneous Aortic Valve Implantation System", Brochure, 8 pages, Copyright 2009.
Medtronic CoreValve™ System, Instructions for Use, 61 pages (2014).
Medtronic, "Loading Heart Valve Catheter", Medical & Scientific Video Production, 59 video screen shots, Copyright 2006.

* cited by examiner

ASSEMBLY AND METHOD FOR LOADING A SELF-EXPANDING COLLAPSIBLE HEART VALVE

CROSS-REFERENCE TO RELATED APPLICATIONS

This application is a continuation of U.S. patent application Ser. No. 14/575,175 filed Dec. 18, 2014, which is a divisional of U.S. patent Ser. No. 13/234,688 filed Sep. 16, 2011, now U.S. Pat. No. 8,973,234, which claims the benefit of the filing date of U.S. Provisional Patent Application No. 61/383,908 filed Sep. 17, 2010, the disclosures of which are hereby incorporated herein by reference.

BACKGROUND OF THE INVENTION

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardium tissue. Such valves are typically fitted within a stent, which may be inserted into the heart at the annulus of the compromised native valve to replace the native valve. To perform such insertion procedure, it is often necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Present crimping devices and methods for collapsing a stented valve, including direct radial assemblies, have proven to be unsatisfactory as they include bulky assemblies, are difficult to master, are time consuming, impart undue stress on the stented valve, or exhibit other undesirable qualities. Moreover, it is sometimes difficult to securely engage the stent to a retaining element of a delivery device. It would therefore be beneficial to provide a device and method for collapsing a stented bioprosthetic heart valve using apparatus and techniques that overcome the deficiencies of conventional devices. In addition, such assembly and method would assist with loading of the collapsed stented valve into a minimally invasive delivery device.

SUMMARY OF THE INVENTION

The present disclosure relates to devices for collapsing a self-expanding prosthetic heart valve. In one embodiment, the device includes a compression member and a pusher member. The compression member has a first open end with a first diameter, a second open end with a second diameter less than the first diameter, and a tapered wall extending between the first open end and the second open end. The tapered wall defines an open space adapted to receive the valve. The pusher member has a base adapted to engage an end of the valve, the pusher member and the compression member being movable relative to one another between an initial position in which the base of the pusher member is relatively far from the first open end of the compression member and an operative position in which the base of the pusher member is relatively close to the first open end of the compression member. Movement of the pusher member and the compression member from the initial position to the operative position pushes the valve through the open space such that the valve is radially compressed by the tapered wall of the compression member as the valve advances through the open space.

The device may further include a first fastener on the pusher member and a second fastener on the compression member, engagement of the first fastener with the second fastener in the operative position securing the pusher member to the compression member. The first fastener may include a plurality of spaced arms extending in a longitudinal direction from the base of the pusher member to a free end. Each of the plurality of arms may extend substantially orthogonally from the base. The free end of each of the plurality of arms may include a first receiving channel oriented in a direction substantially orthogonal to the longitudinal direction. The second fastener may include a base projecting radially outward from the second open end of the compression member and adapted to be received in the first receiving channels in an assembled condition of the pusher member and the compression member.

The compression member may include a rim projecting radially outward from the first open end and adapted to be received between the plurality of arms in an assembled condition of the pusher member and the compression member. Each of the plurality of arms may include a second receiving channel oriented in the longitudinal direction and extending from the free end of the arm toward the base of the pusher member. The first receiving channel may intersect with the second receiving channel on each of the plurality of arms. The compression member may include a plurality of ribs extending in the longitudinal direction between the first open end and the second open end, each rib being adapted to be received in one of the second receiving channels during movement of the pusher member and the compression member from the initial position toward the operative position. The rim of the compression member may include a plurality of recesses, each recess lying between one of the ribs and a remainder of the rim.

The device may further include an annular wall projecting from the base of the pusher member, the annular wall defining a cavity sized and shaped to receive the end of the valve. The annular wall may have an axis of revolution and the pusher member may further include an aperture through the base, a center of the aperture being coincident with the axis of revolution of the annular wall.

The present disclosure also relates to methods for loading a self-expanding prosthetic heart valve into a delivery device, the heart valve having a length, a stent portion formed from a material and at least one retaining member at one end thereof. One method may include inserting the heart valve into a funnel having a first open end with a first diameter and a second open end with a second diameter less than the first diameter; advancing the heart valve through the funnel until the at least one retaining member protrudes out from the second open end of the funnel; attaching the at least one retaining member to a retaining element of the delivery device; advancing a distal sheath of the delivery device over the heart valve to collapse a portion of the heart valve less than the length; cooling the heart valve to a temperature below a transition temperature of the material forming the stent portion of the heart valve; and further advancing the distal sheath of the delivery device over the heart valve until the entire heart valve is collapsed. The collapsed portion of the heart valve may be about one-half or about three-quarters of the length of the heart valve. The heart valve may be cooled by subjecting it to a temperature of about 0° Celsius.

BRIEF DESCRIPTION OF THE DRAWINGS

Various embodiments of the present loading assembly are disclosed herein with reference to the drawings, wherein.

DETAILED DESCRIPTION

Figure 1:
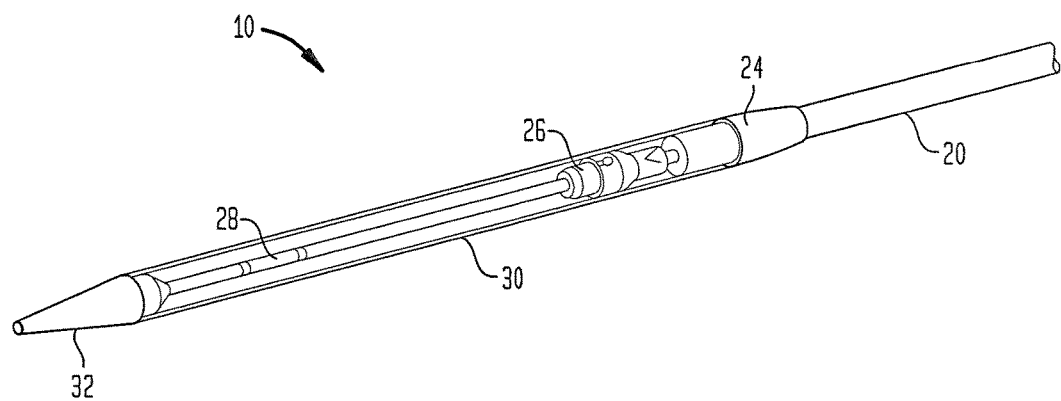
FIG. 1 is a perspective view of a distal portion of a delivery device.

Embodiments of the presently disclosed loading assemblies are described herein in detail with reference to the drawing figures, wherein like reference numerals identify similar or identical elements. In the drawings and in the description which follows, the term "proximal" refers to the end of the loading assembly, or portion thereof, which is closest to the operator in use, while the term "distal" refers to the end of the loading assembly, or portion thereof, which is farthest from the operator in use.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

Figure 2:
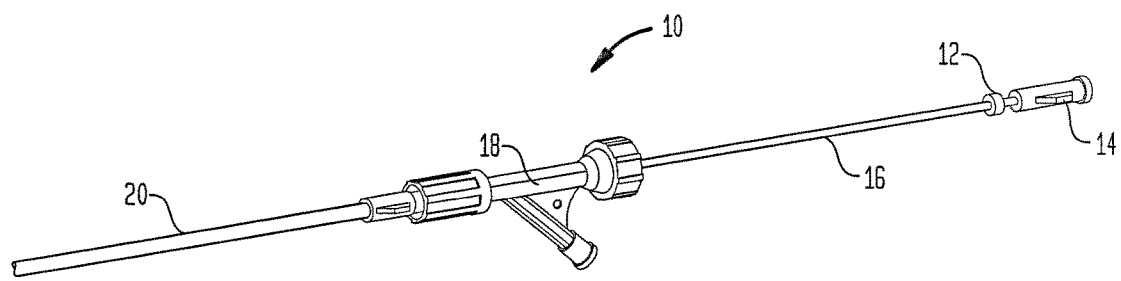
FIG. 2 is a perspective view of a proximal portion of the delivery device of FIG. 1.

As seen in FIG. 2, delivery device 10 may include an inner tube 16 having a lumen extending therethrough. A hub 14 is mounted on the proximal end of the inner tube 16 and is adapted for connection to another system or mechanism, such as a handle, a syringe or a mechanism for displacing the distal sheath 30. Mechanisms for displacing the distal sheath 30 are described in International Patent Application Publication No. WO/2009/091509, the entire contents of which are hereby incorporated herein by reference. A retention ring 12 may also be mounted on the proximal end of the inner tube 16. At least a portion of the inner tube 16 extends through a Y-connector 18 and an outer shaft 20. The Y-connector 18 includes a hemostasis valve for preventing, or at least hindering, blood flow between the inner tube 16 and the outer shaft 20. In addition, the Y-connector 18 may be fluidly coupled to a fluid source.

As shown in FIG. 1, the outer shaft 20 extends to a transition member 24, which may have a tapered shape. The transition member 24 interconnects a distal end of the outer shaft 20 and the distal sheath 30. The distal sheath 30 surrounds a retaining element 26 and a support shaft 28 and can maintain a prosthetic heart valve mounted around the support shaft in a collapsed condition. The support shaft 28 is operatively connected to the inner tube 16 and has a lumen extending therethrough for receiving a guidewire (not shown). The retaining element 26 is mounted on the support shaft 28 and is configured for supporting an end of a prosthetic heart valve or any other suitable medical implant, as discussed in detail below. The retaining element 26 may be longitudinally and rotatably fixed relative to the support shaft 28, thereby preventing the cells of the stent from entangling with one another during deployment. The distal sheath 30 covers the retaining element 26 and at least a portion of the support shaft 28 and is movable relative to the support shaft between a distal position shown in FIG. 1 and a proximal position (not shown). A tip 32 may be connected to the distal end of the support shaft 28, and may have a tapered shape.

Figure 3:
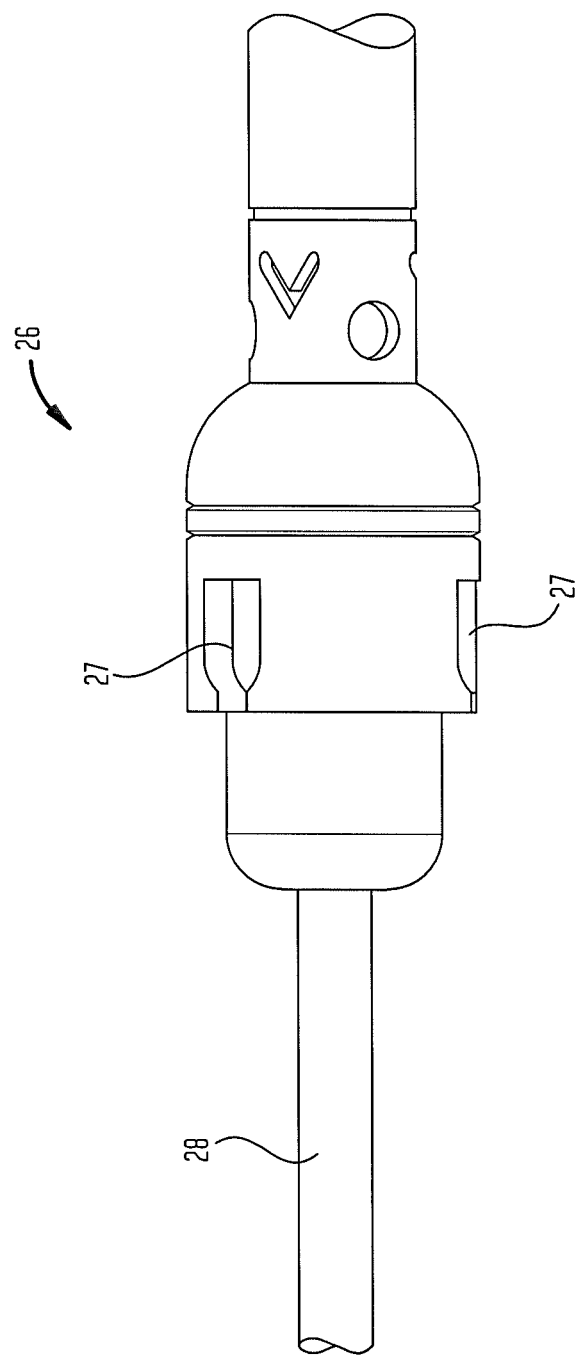
FIG. 3 is an enlarged side view of a retaining element of the delivery device shown in FIGS. 1 and 2.

As shown in FIG. 3, the retaining element 26 is mounted on the support shaft 28 and may be longitudinally and rotatably fixed to same. The retaining element 26 may include a plurality of recesses 27 located around its periphery. The recesses 27 are spaced apart from one another and are adapted and dimensioned to receive a plurality of retaining members or tabs on one end of a self-expanding stent to thereby securely engage such stent to the delivery device. When a self-expanding stent is attached to the retaining element 26, the stent may be longitudinally and rotatably fixed relative to the support shaft 28. As a result, the stent can be prevented from sliding out of the distal sheath 30. In addition, when the distal sheath 30 is placed over the stent to maintain it in the collapsed condition, the cells of the stent will not become tangled.

Figure 4:
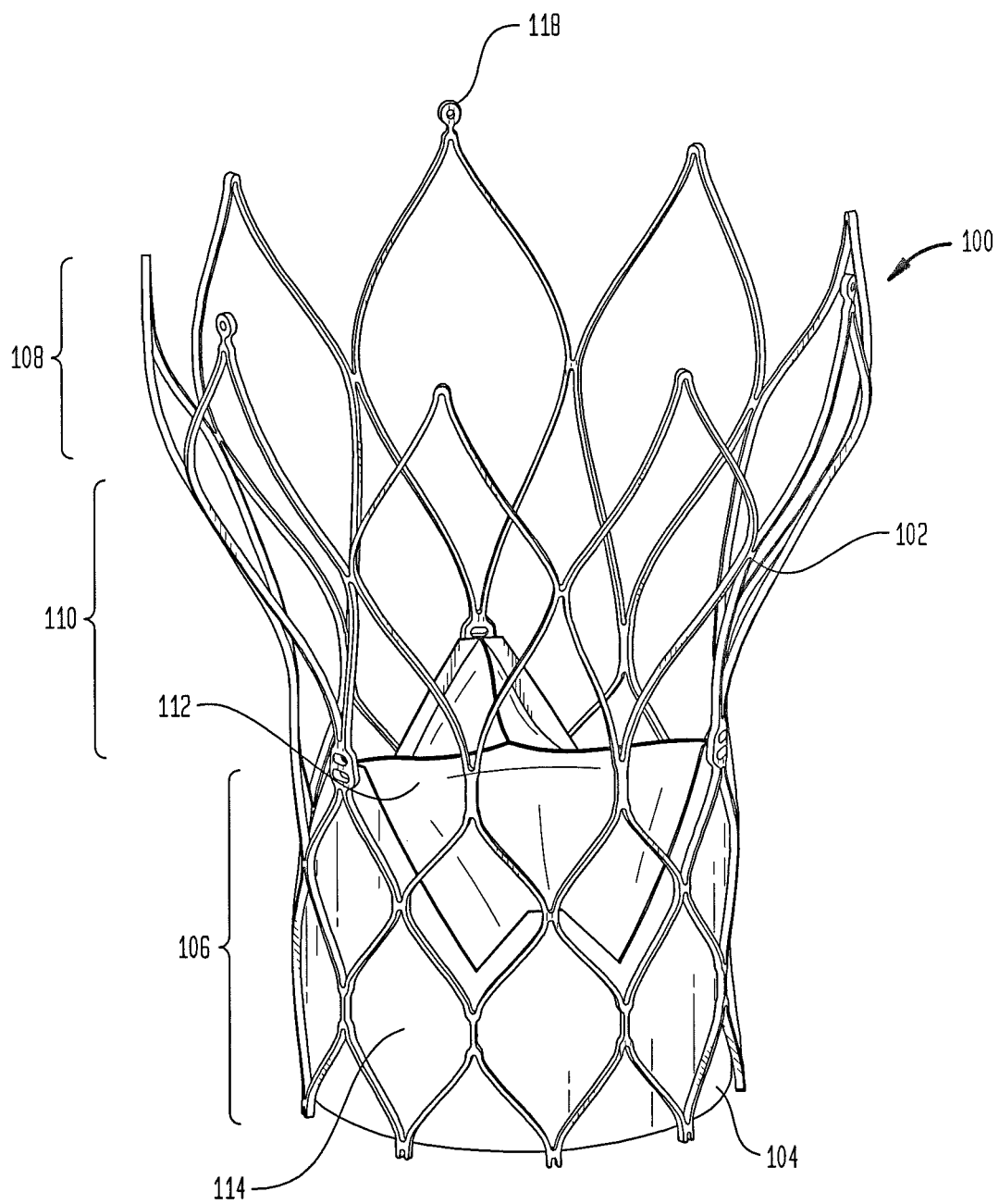
FIG. 4 is a perspective view of a self-expanding prosthetic heart valve.

FIG. 4 shows a bioprosthetic valve 100 designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol, and may include an annulus section 106, an aortic section 108, and an intermediate section 110. The aortic section 108 may have a larger diameter than the annulus section 106. The intermediate section 110 of the stent 102 is located between the annulus section 106 and the aortic section 108. The valve assembly 104 may include a plurality of leaflets 112 and a cuff 114 attached to the stent 102. The leaflets 112 and the cuff 114 may be formed from a biocompatible polymer, from bovine or porcine pericardial tissue, or from other appropriate biocompatible materials. The valve assembly 104 is connected to the stent 102 generally within the annulus section 106, but may extend into the intermediate section 110. The valve 100 may include tabs or retaining members 118 at spaced positions around one or both ends of the stent 102. The retaining members 118 are typically designed for use in loading the valve 100 into a delivery device, in particular for grasping and alignment purposes. However, the retaining members 118 may also be utilized to collapse the valve 100, as will be discussed.

The valve 100 is preferably preserved in its expanded or open condition for storage as the bioprosthetic valve assembly 104 may be compromised by storage in a collapsed condition for extended periods of time. As such, it is necessary to crimp the valve 100 into a collapsed or reduced diameter condition for use in the surgical implantation procedure at the latest possible time before the procedure. In order to effectively limit the time period the valve 100 is collapsed, the crimping process is preferably conducted in the operating arena by the surgeon, interventional cardiologist or surgical assistant using a specialized assembly.

Figure 5:
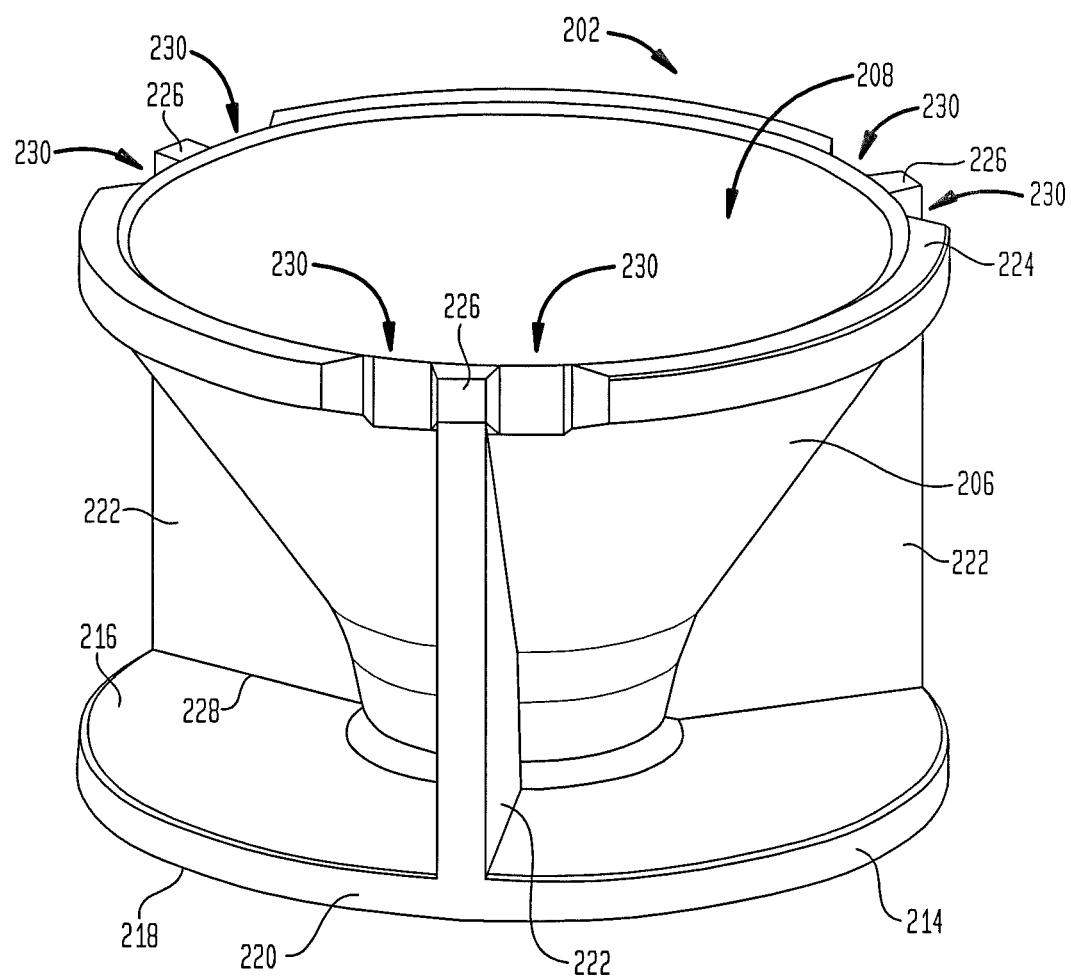
FIG. 5 is a perspective view of a compression member of a loading assembly according to an embodiment of the present invention.
Figure 6:
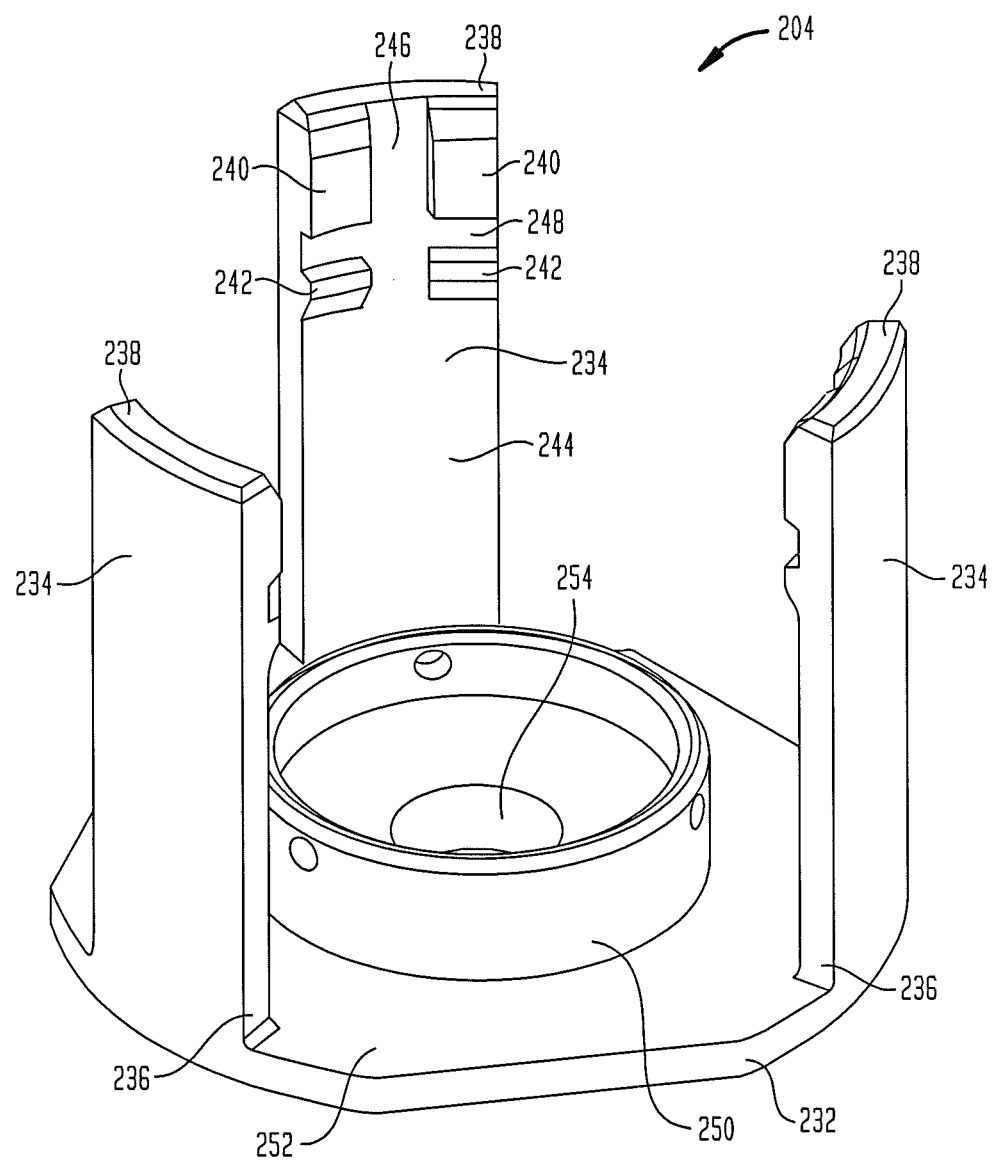
FIG. 6 is a perspective view of a pusher member of a loading assembly according to an embodiment of the present invention.

With reference to FIGS. 5-6, a loading assembly 200 according to an embodiment of the present invention includes a first section or compression member 202 and a second section or pusher member 204 adapted to be connected to one another. As seen in FIG. 5, the compression member 202 includes a funnel 206 for reducing the diameter of a valve. The funnel 206 may have a substantially frusto-conical shape and includes a first open end 208 and a second open end 210. Regardless of the specific shape of the funnel 206, the diameter of the first open end 208 is larger than the diameter of the second open end 210. The diameter of the funnel 206 may decrease uniformly from the first open end 208 to the second open end 210 to compress the valve 100 as it is advanced through the compression member 202.

The compression member 202 may further include a base 214 attached to the outer periphery of the second open end 210 of the funnel 206 for providing stability to the compression member 202 when it is placed on a flat surface. The base 214 may be substantially disk-shaped, with an inner flat surface 216, an outer flat surface 218, and a sidewall 220 extending between the inner surface and the outer surface. The inner surface 216 and outer surface 218 may each have a substantially circular shape, and may be oriented substantially parallel to one another.

In addition to the base 214, the compression member 202 may include a plurality of ribs 222 connected between the outer wall of funnel 206 and the base 214 for enhancing the structural integrity of the loading assembly 200 when the compression member 202 is connected to the pusher member 204. As discussed in detail below, the ribs 222 also facilitate attachment of the compression member 202 to the pusher member 204. The compression member 202 may include three ribs 222 spaced apart from one another around the circumference of funnel 206, although any number of ribs less than or greater than three are contemplated herein. The ribs 222 may be substantially evenly spaced from one another around the circumference of the funnel 206. Each rib 222 may extend from a first end 228 connected to the inner surface 216 of the base 214 to a second end 226 spaced from the first open end 208 of the funnel 206 and may be shaped substantially as a right-angled triangle.

The compression member 202 may further include a rim or lip 224 extending around the circumference of the first open end 208 of the funnel 206. The rim 224 may be discontinuous at recesses 230 to provide clearance for protrusions on pusher member 204, as will be appreciated from the discussion below.

Referring to FIG. 6, the pusher member 204 may include a substantially planar base 232 and a plurality of arms 234 projecting substantially orthogonally from the base. The pusher member 204 may include three arms 234 spaced apart from one another around the periphery of the base 232, although any number of arms less than or greater than three are contemplated herein. Each arm 234 may extend from a first end 236 attached to the base 232 to a free end 238. Each arm 234 may include any suitable locking feature, such as protrusions 240, 242 on its inner surface 244, for locking the pusher member 204 to the compression member 202. The protrusions 240, 242 may be located near the free end 238 of each arm 234. The protrusions 240, 242 collectively form a first channel 246 extending in the longitudinal direction of each arm 234 and a second channel 248 extending substantially orthogonally to the first channel 246 in the width direction of each arm 234. Each longitudinal channel 246 may extend between two protrusions 240 and two protrusions 242 in a central location along the inner surface 244 of each arm 234, and is adapted and dimensioned to receive at least a portion of a rib 222 of the compression member 202. As discussed in detail below, the longitudinal channels 246 of the pusher member 204 and the ribs 222 of the compression member 202 cooperate with one another to facilitate sliding movement of the pusher member 204 longitudinally relative to the compression member 202. Each widthwise channel 248 on arms 234 may extend between two protrusions 240 and two protrusions 242 and is adapted and dimensioned to receive the base 214 of the compression member 202. When the base 214 of the compression member 202 is positioned within the widthwise channels 248 in the arms 234 of the pusher member 204, the pusher member 204 is longitudinally fixed to the compression member 202.

The base 232 of the pusher member 204 may include an aperture 254 disposed through the approximate center thereof with an annular wall or ring 250 attached to an inner surface 252 of the base around the aperture. The annular wall 250 is adapted and dimensioned to receive at least a portion of the annulus section 106 of the stent 102, as seen in FIG. 7.

Figure 7:
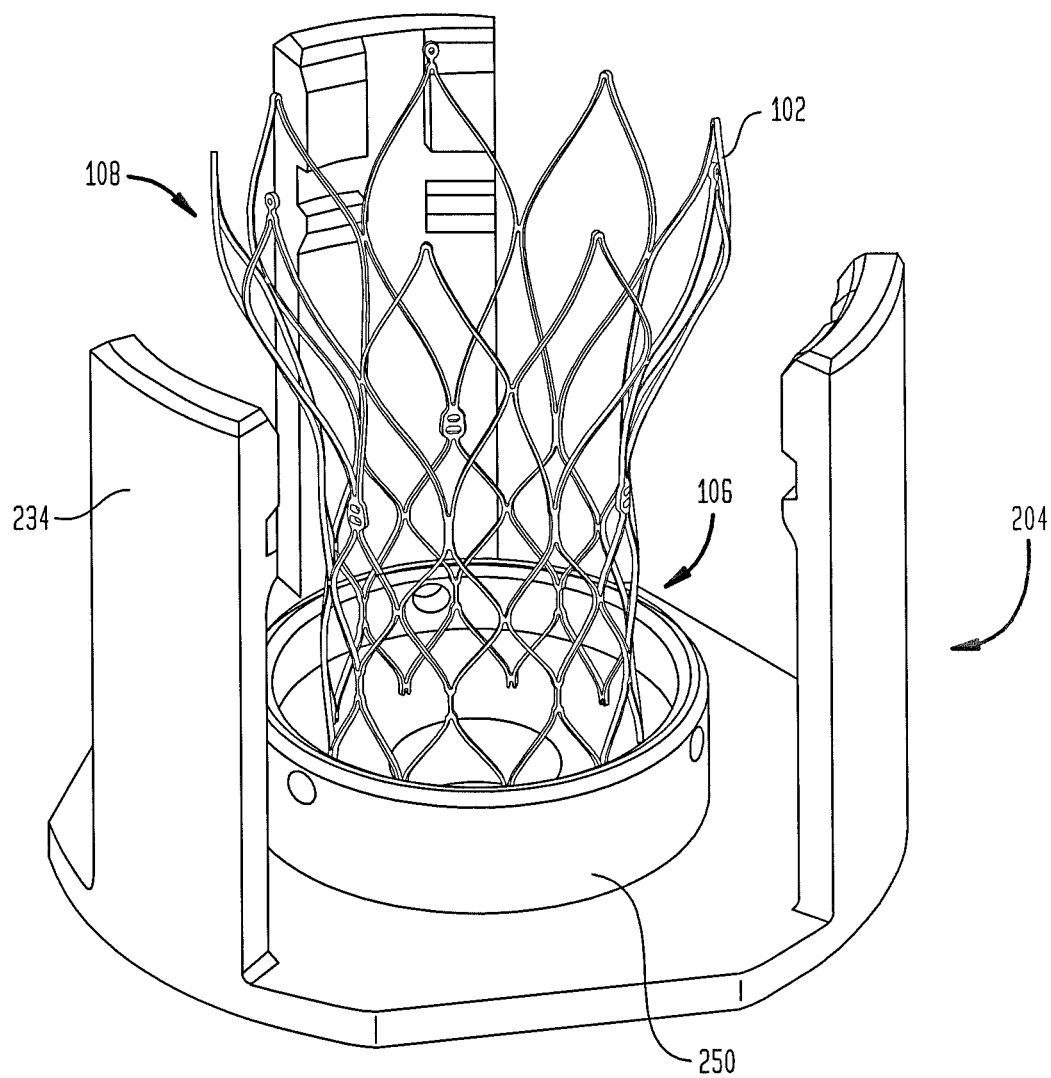
FIG. 7 is a perspective view of the pusher member of FIG. 6 with a stent positioned therein.
Figure 8:
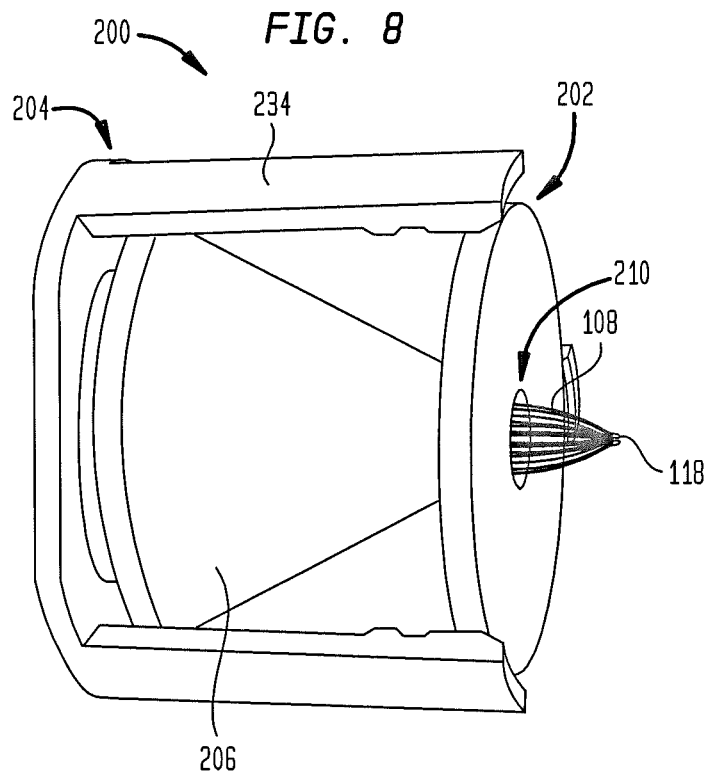
FIGS. 8 and 9 illustrate an exemplary method of using the loading assembly shown in FIGS. 5 and 6.
Figure 9:
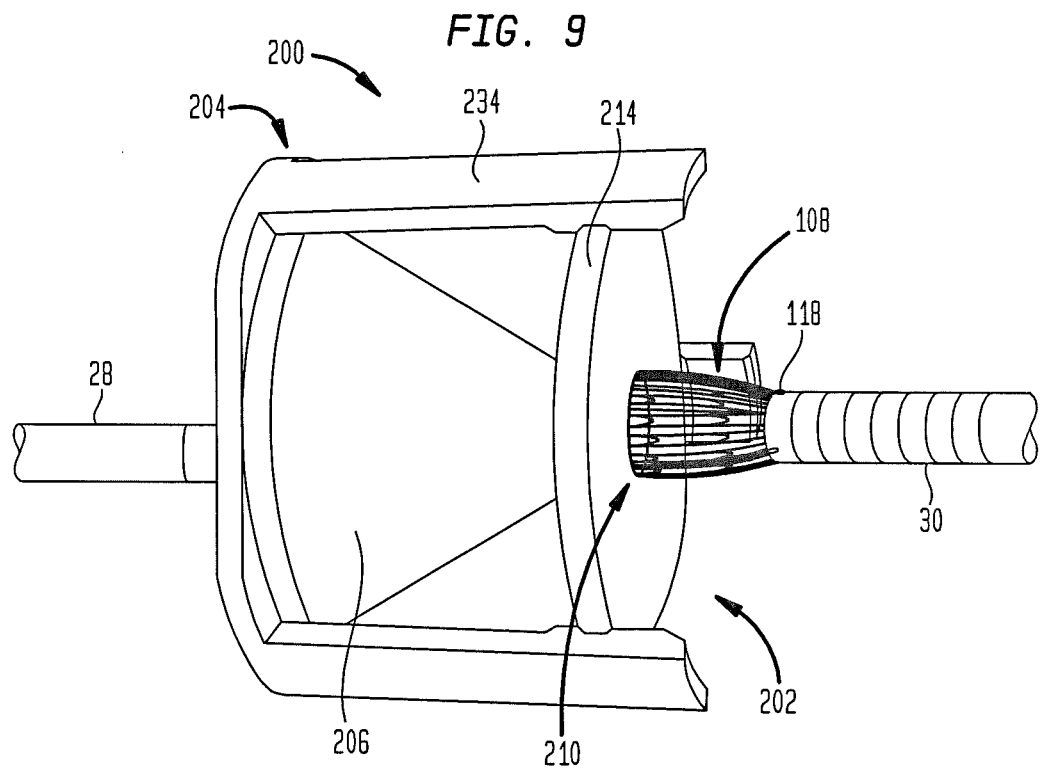

As seen in FIGS. 7-9, the loading assembly 200 may be used to load the collapsible prosthetic heart valve 100 into a delivery device. With the pusher member 204 on a flat surface, at least a portion of the annulus section 106 of the stent 102 may be placed within the confines of the annular wall 250. At this point, the annulus section 106 may contact the inner surface of the annular wall 250. The compression member 202 may then be inverted over the aortic section 108 of the stent 102 so that the aortic section of the stent is positioned within the funnel 206 and the ribs 222 of the compression member are axially aligned with the longitudinal channels 246 in arms 234. The pusher member 204 and compression member 202 may then be pushed together, with the tapered walls of the funnel 206 gradually compressing the valve 100, until a portion of the aortic section 108 of the stent 102 passes through the second open end 210 of the funnel, as shown in FIG. 8. As the pusher member 204 and the compression member 202 are pushed together, the protrusions 240 242 on arms 234 may slide freely through the recesses 230 in rim 224 as the ribs 222 slide within the longitudinal channels 246. When a portion of the aortic section 108 passes through the second open end 210 of the funnel 206, the retaining members 118 of the stent 102 will protrude through the open end 210 of the funnel and will be positioned closely adjacent to one another. Continued movement of the pusher member 204 and the compression member 202 toward one another further compresses the valve 100 and exposes more portions of the stent 102 out through open end 210, causing the retaining members 118 to separate from one another. The pusher member 204 and the compression member 202 may be pushed together until the base 214 of the compression member rides over the protrusions 240 of the pusher member, temporarily flaring out the arms 234, until the base snaps into place in the widthwise channel 248 in each arm. The lengths of compression member 202 and arms 234 are such that base 214 will become engaged in channels 248 before the rim 224 of the compression member contacts the inner surface 252 of the base of the pusher member. The engagement of base 214 in the channels 248 longitudinally fixes the pusher member 204 to the compression member 202. The tip 32 and the support shaft 28 of delivery device 10 may then be inserted into the end of the collapsed valve 100 protruding through the first open end 210 of the funnel 206, through the collapsed valve, and out through the aperture 254 in the pusher member 204, as shown in FIG. 9. The retaining members 118 of the stent 102 may be positioned over the retaining element 26 of the delivery device 10 and within the recesses 27 thereof, thereby attaching the stent 102 to the delivery device. The distal sheath 30 of the delivery device may then be moved over the valve 100 until the valve is completely covered.

In view of the tight fit between the collapsed valve 100 and the distal sheath 30, significant frictional forces must be overcome in order to move the distal sheath completely over the valve. In order to facilitate this procedure, the stent 102 may be substantially cooled which, based on the materials forming the stent, enables the stent to more easily deform. Thus, once more than about one-half of the length of stent 102 has been covered by the distal sheath 30, the entire assembly, including the distal end of the delivery device 10 and the loading assembly 200, may be immersed in a cold liquid, such as a saline solution. The assembly may then be removed from the liquid, and the distal sheath 30 moved further over the valve 100 until it completely covers same.

Rather than immersing the entire assembly, including the loading assembly 200, in the cold liquid, the loading assembly may first be separated from the delivery device 10. To accomplish this, the user may pull the pusher member 204 and the compression member 202 apart until the arms 234 flare outwardly and enable the base 214 to slide past the protrusions 240. The pusher member 204 and the compression member 202 may then be separated, permitting removal of the delivery device 10.

As discussed above, the stent 102 may be substantially cooled to make it easier to be completely covered with the distal sheath 30 of the delivery device 10. In this regard, the stent 102 should be cooled to temperatures below the transition temperature of the material forming the stent 102. The "transition temperature" is the temperature at which a material changes from one crystal state to another. For the nitinol stents that may be employed in the present invention, a saline solution at about 0° C. may be used. When cooled below its transition temperature, the stent 102 becomes plastic, enabling it to deform much more readily under the forces exerted by the movement of the distal sheath thereover. Accordingly, after cooling the stent 102 below the transition temperature, the user may completely cover the stent with the distal sheath 30 of the delivery device 10.

Figure 10:
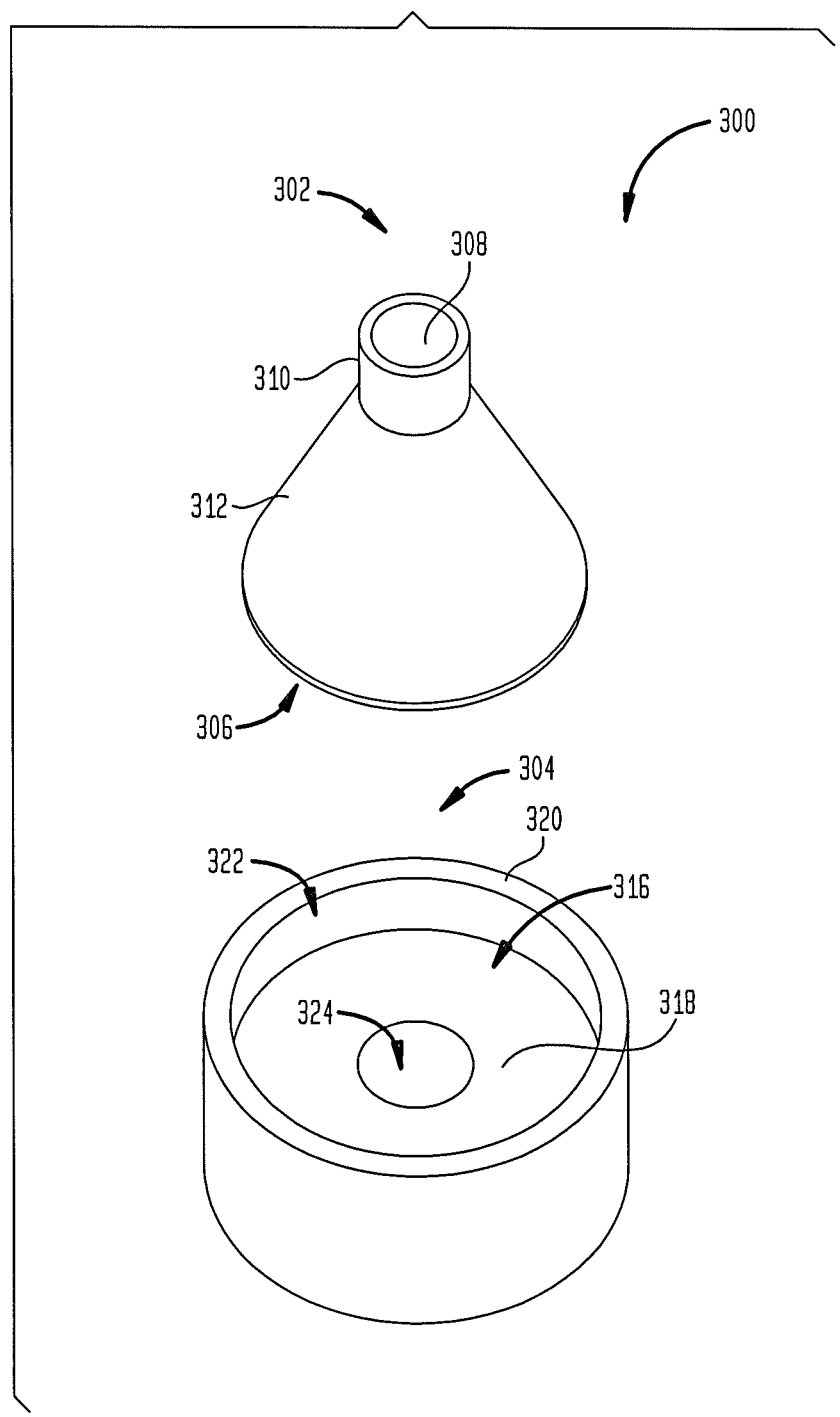
FIG. 10 is a perspective view of a loading assembly according to another embodiment of the present invention.

FIG. 10 depicts a loading assembly 300 in accordance with another embodiment of the present invention. The loading assembly 300 includes a funnel 302 with a first open end 308 and a second open end 306 disposed in communication with one another. The funnel 302 has a proximal portion 310, which may have a substantially cylindrical shape, and a distal portion 312 which has a tapered shape with multiple diameters along its length. The distal portion 312 of the funnel 302 may have a frusto-conical shape, so that its diameter at the second open end 306 of the funnel 302 is larger than the diameter adjacent to the proximal portion 310.

The loading assembly 300 further includes a pusher member 304 having a cavity 316 adapted and dimensioned to receive at least the second open end 306 of the funnel 302. The cavity 316 of the pusher member 304 is defined by an inner flat surface 318 and an annular wall 320. The annular wall 320 may completely encircle the cavity 316. An open end 322 of the cavity 316 is also adapted and dimensioned to receive at least the second open end 306 of the funnel 302. An aperture 324 may extend through the pusher member 304 along the central longitudinal axis thereof.

Figure 11:
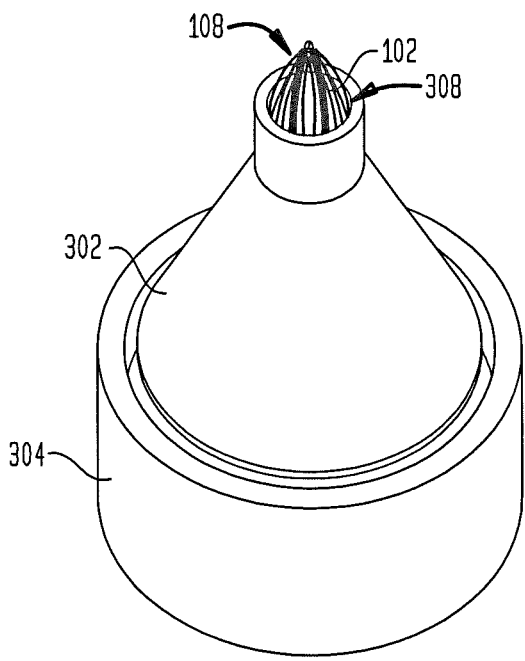
FIGS. 11 and 12 illustrate the initial steps of a method for loading a prosthetic heart valve into a delivery device using the loading assembly of FIG. 10.
Figure 12:
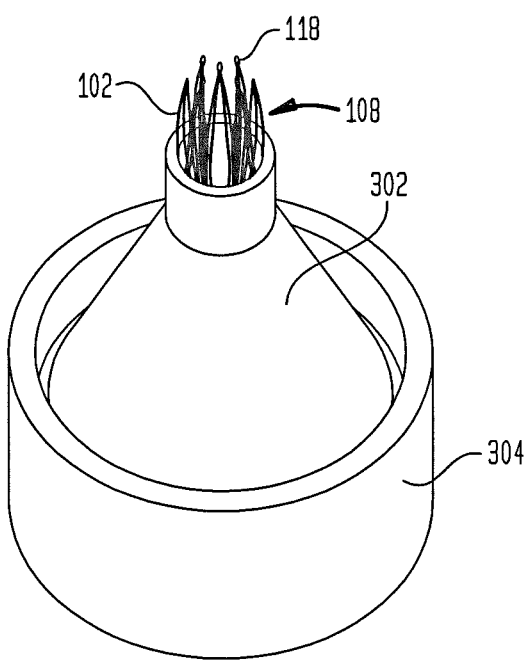

With reference to FIGS. 11, 12, and 13A-13D, the loading assembly 300 may be used to load a valve 100 into a delivery device. To load the valve 100 in the delivery device, at least a portion of the annulus section 106 of the stent 102 may be positioned within the cavity 316 of the pusher member 304. The annulus section 106 of the stent 102 should be in contact with the inner surface 318 of the pusher member 304. The funnel 302 may then be placed over the stent 102, as shown in FIG. 11, so that the tapered wall of the distal portion 312 gradually compresses the valve and at least a portion of the aortic section 108 of the stent passes through the first open end 308 of the funnel. The user may push the funnel 302 down toward the pusher member 304 to compress more of the stent 102 and push it through the open end 308 of the funnel 302. As a greater length of the compressed stent 102 is exposed through the open end 308 of the funnel 302, the retaining members 118 will separate from one another, as seen in FIG. 12.

Figure 13A:
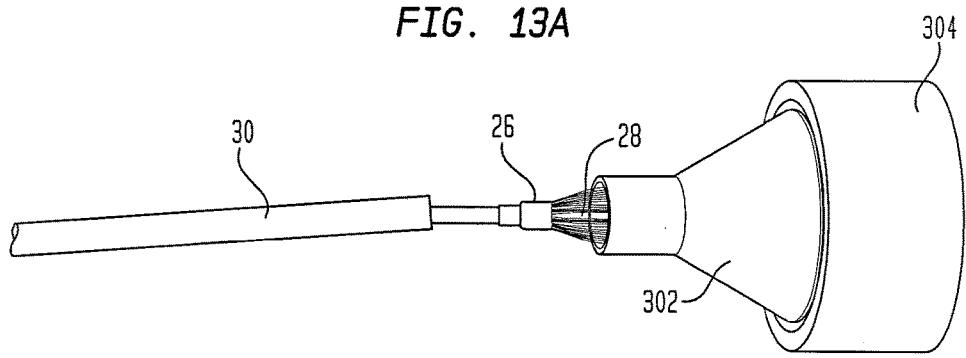
FIGS. 13A-13D illustrate further steps of the method for loading a prosthetic heart valve into a delivery device using the loading assembly of FIG. 10.

As illustrated in FIG. 13A, the support shaft 28 of the delivery device 10 may be inserted between the retaining members 118 of the stent 102 and through the first open end 308 of the funnel 302. The retaining members 118 of the stent 102 may then be positioned over the retaining element 26 of the delivery device 10 and within the recesses 27 thereof, thereby attaching the stent to the delivery device 10.

Figure 13B:
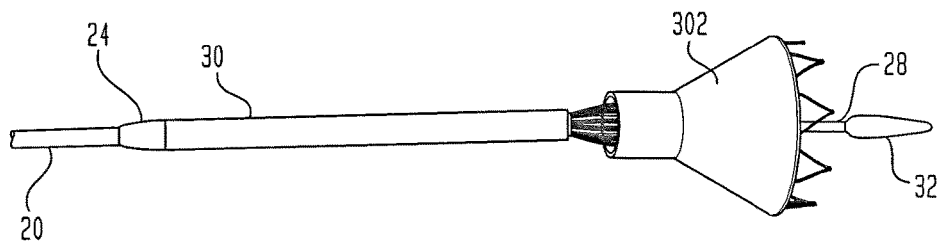
Figure 13C:
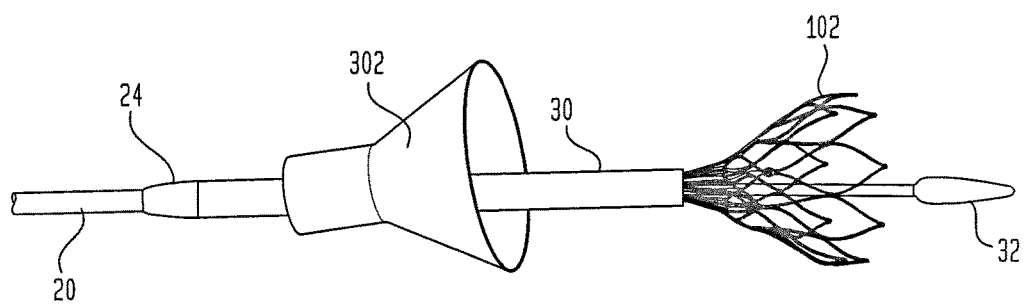
Figure 13D:
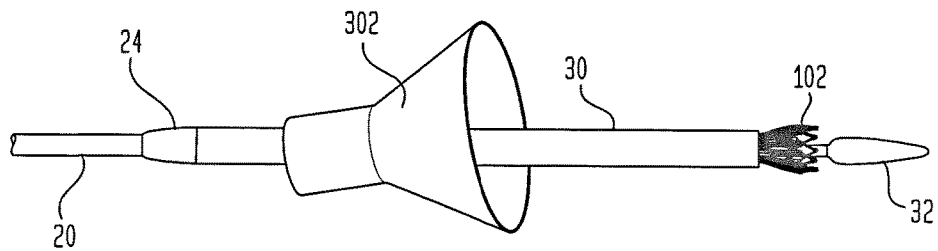

After the stent 102 has been attached to the delivery device 10, the user may move the pusher member 304 away from the stent while maintaining the funnel 302 in place, as seen in FIG. 13B. The distal sheath 30 may then be advanced toward the stent 102 to cover the retaining element 26 and at least about one-half of the length of the stent, as depicted in FIG. 13C. At this point, the funnel 302 may be moved over the distal sheath 30 and away from the stent 102. The distal sheath 30 may be further advanced to cover almost the entire stent 102 (e.g., about three quarters of the length of the stent). The stent 102 may then be substantially cooled as discussed above (e.g., to a temperature below the transition temperature of the material forming the stent) to convert the stent to a state exhibiting plastic properties. Such plastic properties enable the stent 102 to more readily deform as the distal sheath 30 is moved over same. Once the entire stent 102 has been covered by the distal sheath 30, the funnel 302 may be removed from the delivery device 10.

FIGS. 14A-14B and 15A-15D show an alternate method of using the loading assembly 300 to load the stent 102 into a delivery device. Aside from the loading assembly 300, this exemplary method employs a holding tube 400 having a lumen 402 extending therethrough. The diameter of the holding tube 400 preferably is slightly smaller than the inner diameter of the proximal portion 310 of the funnel 302, such that the holding tube fits within the proximal portion of the funnel.

Figure 14A:
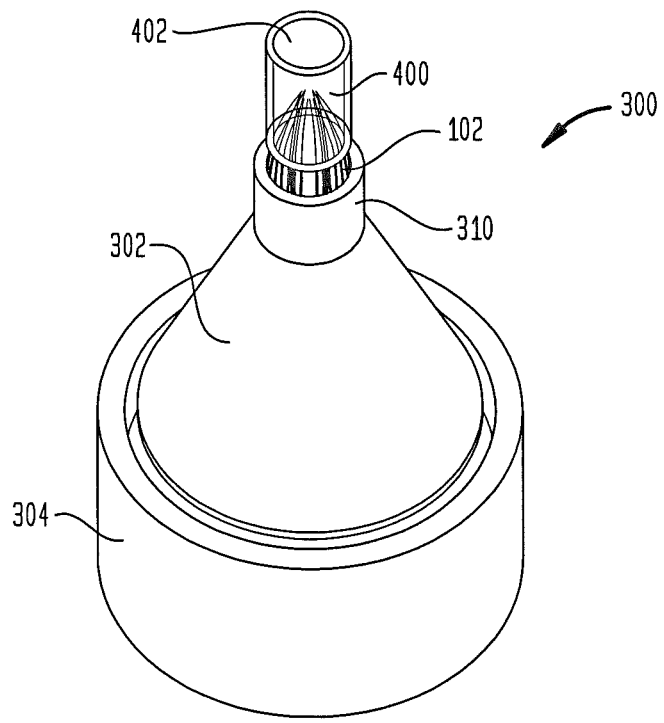
FIGS. 14A and 14B illustrate steps of an alternate method of loading a prosthetic heart valve into a delivery device using the loading assembly of FIG. 10 and a tube.
Figure 14B:
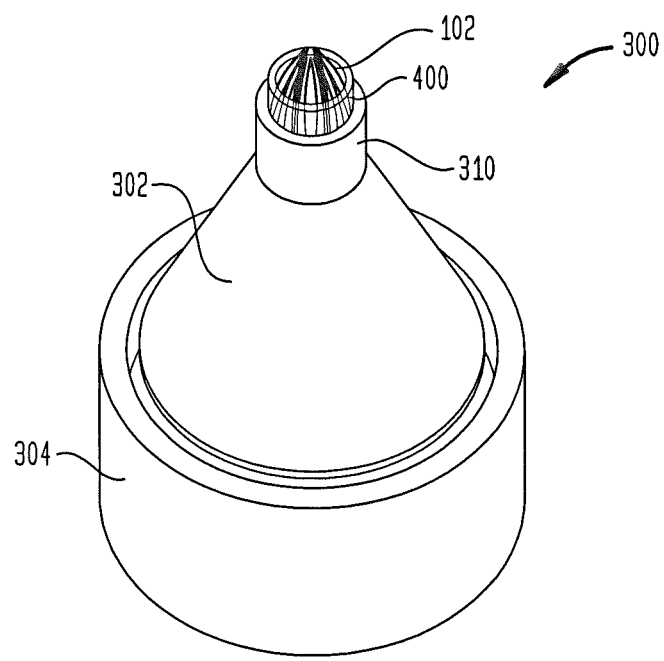

As seen in FIG. 14A, the stent 102 may be initially compressed with the loading assembly 300, as described above. In this method, however, the holding tube 400 is positioned over the portion of the stent 102 (e.g., at least a portion of the aortic section 108) protruding from the funnel 302. The holding tube 400 may be advanced toward the pusher member 304, such that the holding tube is positioned within the proximal portion 310 of the funnel 302, as seen in FIG. 14B. At this point, the holding tube 400 maintains at least a portion of the stent 102 in a collapsed condition.

Figure 15A:
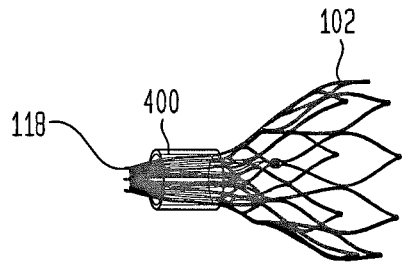
FIGS. 15A-15D illustrate additional steps of the alternate method of loading a prosthetic heart valve into a delivery device using the loading assembly and the tube shown in FIGS. 14A and 14B.
Figure 15B:
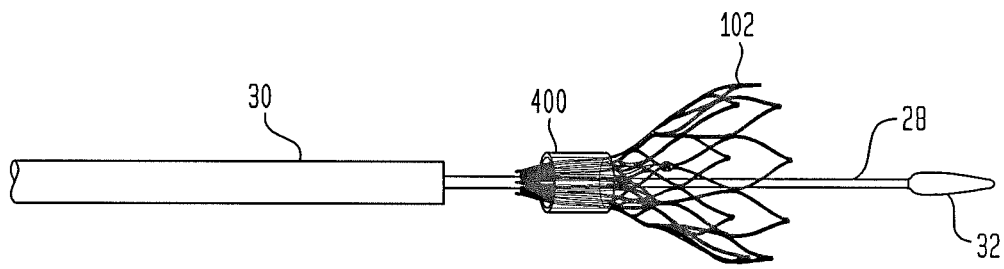
Figure 15C:
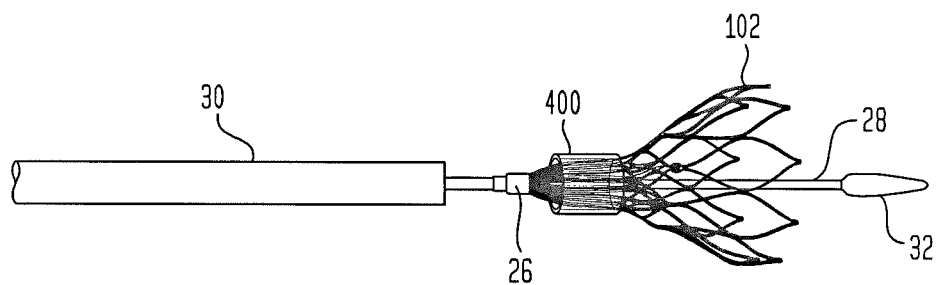
Figure 15D:
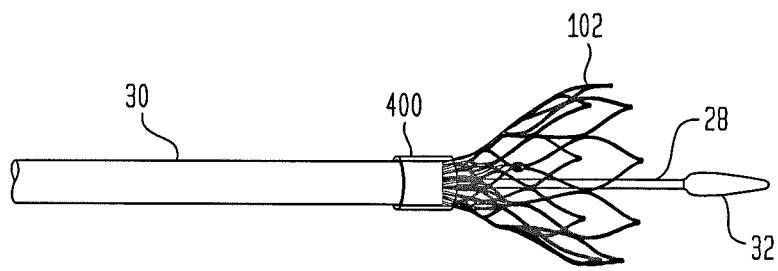

The funnel 302 and the pusher member 304 may then be separated from the stent 102, as shown in FIG. 15A. Thereafter, the tip 32 and support shaft 28 of the delivery device 10 may be is inserted through the stent 102, beginning from the collapsed end thereof, as seen in FIG. 15B, until the retaining members 118 of the stent are positioned in the recesses 27 of the retaining element 26, as shown in FIG. 15C. The distal sheath 30 may then be advanced toward the tip 32 to cover at least a portion of the stent 102. For example, the distal sheath 30 may cover more than one-half of the length of the stent 102 or more than three quarters of the length of the stent at this point. As the distal sheath 30 is advanced, the holding tube 400 may be moved over the distal sheath 30, as seen in FIG. 15D. Once the stent 102 has been largely covered by the distal sheath 30 (e.g., about three quarters of the length of the stent), the user may substantially cool the stent as described above, to render the stent 102 more plastic. This step will enable the user to more readily move the distal sheath 30 toward the tip 32 to cover the entire stent 102. Once the stent 102 has been largely or entirely covered by the distal sheath 30, the holding tube 400 may be removed.

Figure 16:
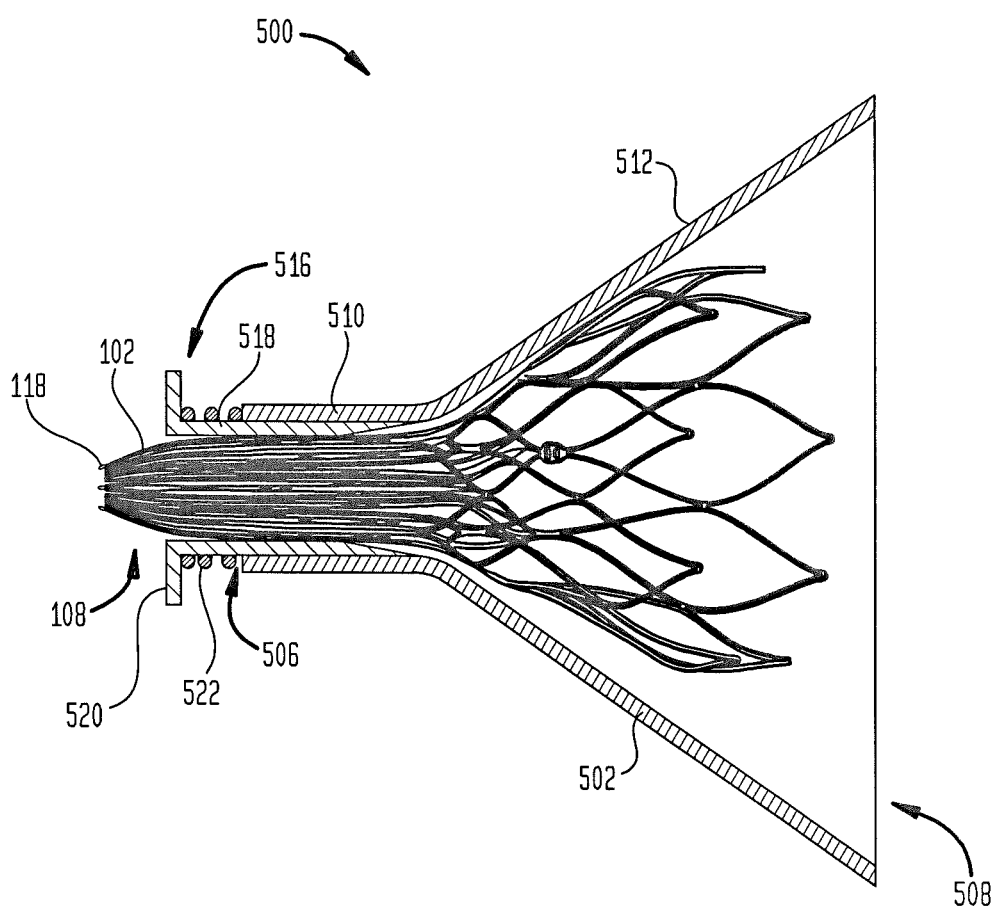
FIG. 16 is a loading system according to an alternate embodiment of the present invention.

FIG. 16 shows a loading assembly 500 according to yet another embodiment of the present invention. The loading assembly 500 includes a funnel 502 with a first open end 506 and a second open end 508 disposed in communication with one another. The proximal portion 510 of the funnel 502 has a substantially cylindrical shape, while the distal portion 512 of the funnel 502 has a tapered shape with multiple diameters along its length. The distal portion 512 of the funnel 502 may have a substantially frusto-conical shape, so that its diameter at the second open end 508 is larger than its diameter next to the proximal portion 510. The tapered shape of the distal portion 512 compresses a valve 100 passing therethrough.

The loading assembly 500 further includes an adjustable member 516 movable relative to the funnel 502. The adjustable member 516 includes a substantially cylindrical body 518 having an outer diameter which is slightly smaller than the inner diameter of the proximal portion 510 of the funnel 502. Accordingly, the body 518 of the adjustable member 516 can slide within the proximal portion 510 of the funnel. A flange 520 provided at one end of the body 518 has a diameter substantially similar to or larger than the outer diameter of the proximal portion 510 of the funnel 502. The flange 520 serves as a mechanical stop, preventing the adjustable member 516 from being inserted completely within the proximal portion 510 of the funnel 502. A biasing member interposed between the flange 520 and the free end of the proximal portion 510 of the funnel 502 biases the adjustable member 516 away from the funnel. One such preferred biasing member is a spring 522 assembled around the body 518 of the adjustable member 516. The spring 522 or other biasing member may be used to more precisely control the amount by which the aortic section 108 of the stent 102 protrudes from the adjustable member 516, and thus the separation between the retaining members 118 of the stent before inserting the tip 32 and support shaft 28 of the delivery device 10 through the valve 100.

The loading assembly 500 may be used to load a valve 100 into delivery device 10 in substantially the same way as loading assembly 300 described above, including the use of a pusher member similar to pusher member 304. When using loading assembly 500, however, the user can more precisely control the separation between the retaining members 118. For example, the user may move the adjustable member 516 toward the funnel 502 to expose a greater length of the stent 102, thereby allowing the retaining members 118 to achieve more separation from one another. Conversely, the user may move the adjustable member 516 away from the funnel 502 to move the retaining members 118 closer to one another for assembly in the recesses 27 of the deployment device retainer 26.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for collapsing a self-expanding prosthetic heart valve, comprising:
    a compression member having a first open end with a first diameter, a second open end with a second diameter less than the first diameter, and a tapered inner wall decreasing uniformly in diameter between the first open end and the second open end, the tapered inner wall defining an open space adapted to receive the valve, the compression member having a fixed length between the first open end and the second open end; and
    a pusher member having a base adapted to engage an end of the valve, the pusher member and the compression member being movable relative to one another between an initial position in which the base of the pusher member is relatively far from the first open end of the compression member and an operative position in which the base of the pusher member is relatively close to the first open end of the compression member, wherein movement of the pusher member and the compression member from the initial position to the operative position pushes the valve through the open space such that the valve is radially compressed by the tapered inner wall of the compression member as the valve advances through the open space.

2. The device of claim 1, wherein the pusher member includes an annular wall projecting from the base, the annular wall defining a cavity sized and shaped to receive the end of the valve.

3. The device of claim 2, wherein the annular wall has an axis of revolution and the pusher member further includes an aperture through the base, a center of the aperture being coincident with the axis of revolution of the annular wall.

4. The device as claimed in claim 1, wherein the compression member includes a cylindrical extension at the second open end, the cylindrical extension having the second diameter.

5. The device as claimed in claim 1, further comprising a holding tube removably insertable in the second open end of the compression member.

6. The device as claimed in claim 5, wherein the holding tube has a cylindrical configuration with a diameter less than the second diameter.

7. The device as claimed in claim 1, further comprising an adjustable member including a body having first and second ends and a transverse cross-section less than the second diameter, and a flange at the second end of the body, the flange having a transverse cross-section larger than the second diameter, the body being slidable within the second open end of the compression member.

8. The device as claimed in claim 7, further comprising a biasing member interposed between the flange and the second open end of the compression member to bias the flange away from the second open end of the compression member.

9. The device as claimed in claim 8, wherein the biasing member comprises a spring assembled around the body of the adjustable member.

\* \* \* \* \*